United States Patent [19]

Bago

[11] 4,168,313

[45] Sep. 18, 1979

[54] PHTHALIDYL 2-(3'-TRIFLUOROMETHYL-ANILINO)-PYRIDINE-3-CARBOXYLATE AND ITS SALTS

[76] Inventor: Sebastian Bago, Bernardo de Irigoyen 248, Buenos Aires, Argentina

[21] Appl. No.: 879,749

[22] Filed: Feb. 21, 1978

[51] Int. Cl.² .................... C07D 213/55; A61K 31/44
[52] U.S. Cl. ..................................... 424/266; 546/269
[58] Field of Search ..................... 260/295.5 B, 295 F, 260/295.5 R; 424/266; 546/269

[56] References Cited

U.S. PATENT DOCUMENTS 3,478,040  11/1969  Sherlock ..................... 260/295.5 R
3,959,272  5/1976  Hoffman ..................... 260/295.5 R Primary Examiner—Alan L. Rotman
Attorney, Agent, or Firm—Kane, Dalsimer, Kane, Sullivan and Kurucz

[57] ABSTRACT

A new phthalidylic eater of 2-(3'trifluoromethylanilino)-pyridine-3-carboxylic acid is prepared by reacting 2-(3'-trifluoromethylanilino)-pyridine-3-carboxylic acid with 3-bromophthalide and an organic base in a reaction medium comprising a solvent selected from the group consisting of acetone, dimethylformamide, dimethylacetamide and acetonitrile. The product has an antiinflammatory activity without the ulcerogenic effect that is characteristic of the corresponding acid.

14 Claims, No Drawings

PHTHALIDYL 2-(3'-TRIFLUOROMETHYL-ANILINO)-PYRIDINE-3-CARBOXYLATE AND ITS SALTS

This invention relates to phthalidylic 2(3'-trifluormethylanilino) pyridine-3-carboxylate or the 2(3'-trifluormethylphenylamino)-nicotinic acid phthalidylic ester of formula I, and pharmaceutically acceptable salts thereof

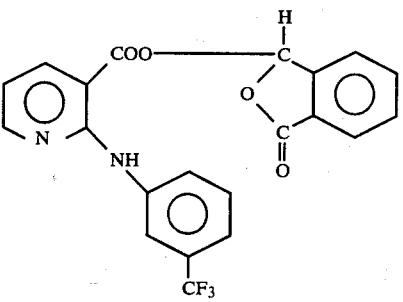

Among its organic and inorganic acid salts the hydrochloride is preferably use.

With the introduction of substituted N-arylanthranilic acids in the antiinflammatory therapy (Winder, C. V. et al., J. Pharmacol. Exp. therap., 138, 1195, 1962) a wide variety of derivatives and analogs were developed. On the research of analogs of said acids, also named fenamic acids (mefenamic, flufenamic, meclofenamic acids), are deducing from structure-activity relationship for the N-aryl-anthranilic acids that the substitution in the anthranilic ring and the ortho position of the carboxyl are critical for antiinflammatory activity (Scherrer R. A. et al. 9th Nat. Med. Chem. Symp. Am. Chem. Soc. 1964, Abstr. IIa-IIi 1964), the substituted 2-anilino-pyridine-3-carboxylic acids were developed. Belonging from them is the 2(3'-trifluormethylanilino) pyridine-3-carboxylic acid. This acid, as well as the fenamic acids has a relevant antiinflammatory activity, but also provoke ulcers.

This application is related to a new ester of said acid with anti-inflammatory activity and without ulcerogenic effect. Specifically it refers to phthalidyl ester thereof.

Phthalidyl 2-(3'-trifluormethylanilino)-pyridin-3-carboxylate can be obtained following this synthesis' scheme:

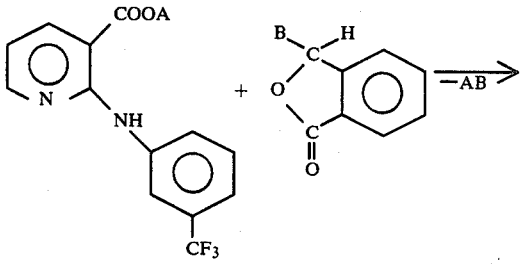

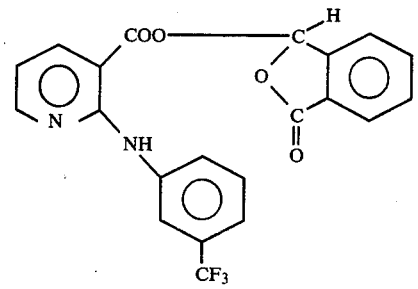

where A, from the 2(3'-trifluormethylanilino) pyridine-3-carboxylate group, can be hydrogen or a base, and B, from the phthalidylic group, can be an hydroxy, alkylsulfonyloxi, arylsulfonyloxy or an halogen group.

In this invention, the 2(3'-trifluormethylanilino) pyridine-3-carboxylic acid is used. Techniques and patents literature on the synthesis of this acid were widely published (British patent No. 1,064,259; South African Patent No. 6,703,522; Argentine Patent Nos. 179.702 and 182.409; Hoffman C. and Faure A., Bull. Soc. Chim. Franc., 2136, 1966.

To obtain the new compound, this acid was reacted with a substituted phthalide in presence of bases as proton-acceptor, or can be previously salified with inorganic or organic bases, having the formula

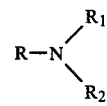

where $R$, $R_1$, $R_2$ can be independently hydrogen, aryl, alkyl or aliphatic alcohol radicals. Bases solubles in the reaction medium were used. Among them: diethylamine, diethanolamine, benzylamine, cyclohexylamine, preferably triethylamine. This reaction was performed at room temperature. On the other hand, the selected phthalide was 3-bromophthalide, compound obtained halogenating the phthalide with N-bromosuccinimide in presence or absence of catalysts, in hydrous carbon tetrachloride (Org. Synth, 42, 1962). Its condensation with 2-(3'-trifluormethylanilino)-pyridine-3-carboxylic acid, was performed in a reaction medium consisting in a solvent or mixture of solvents where the formed compound is perfectly soluble. The selected solvents were: acetone, dimethylformamide, dimethylacetamide and-/or acetonitrile. One of the advantages of this reaction is based on the fact, that this reaction is performed in the same reaction medium where the salification is done. As 3-bromophthalide is decomposed to phthalaldehydic acid in presence of water (Org. Synth. Coll. Vol. 3, 737, 1955), consequently it was necessary to use with preference anhydrous solvents. Thus, anhydrous solvents or the mixture of them gave the best yields. The reaction was performed at a temperature range between: 20° and 60° C.

The separation of the formed compound was done pouring the reaction mixture into water and filtering the precipitated phthalidyl 2-(3'-trifluormethylanilino)-pyridine-3-carboxylate.

Another employed alternative was to extract the formed compound, from its reaction mixture, by means of water immiscible solvents, crystallisation and subsequent filtration of phthalidyl 2-(3'-trifluormethylanilino)-pyridine-3-carboxylate. The solvent preferably used in this extraction was ethyl acetate.

The process of preparation of the phthalidyl 2-(3'-trifluormethylanilino)-pyridine-3-carboxylate salt, such as the hydrochloride or hydrobromide, was performed dissolving the ester in ethyl acetate, and adding hydrochloric or hydrobromic acid, which was previously dissolved in a low molecular weight aliphatic alcohol mixed with ethyl acetate, preferably isopropanol.

With this new compound, phthalidyl 2-(3'-trifluormethylanilino)-pyridine-3-carboxylate, pharmacological assay were performed.

1 By means of the test involving the carraghenine-provoked aedema of the paw of rat (Winter, C. A., Proceeding Soc. Exp. Biol. Med., III, 544, 1962) the antiinflammatory activities of phthalidyl 2-(3'-trifluormethylanilino)-pyridine-3-carboxylate (PTP) and 2(3'-trifluormethylanilino) nicotinic acid (TNA), were compared.

The obtained results are shown in the following table:

| COMPOUND | DOSIS mg/Kg weight | % AEDEMA INHIBITION 3 hr | 4 hr |
|---|---|---|---|
| TNA | 47 | 25.6 | 31.8 |
| PTP | 69 * | 32 | 37.8 |

* Equivalent to 47 mg of 2(3'-trifluormethylanilino) pyridine-3-carboxylic acid.

2 To compare the effect on ulcer of the new compound regarding to other antiinflammatory drugs, the method of Goldemberg (ulceration by pylorus ligature) (Arzneim. Forsch. (Drug Res.) 26, 3, 1976) to Sprague-Dowley rats (400–600 g of weight), was performed. The ulceration of the gastric epithelium was observed and evaluated in accordance to the following score; 0=no hemorrhagic spots; 1=some isolated hemorrhagic spots; 2=redness of the gastric epithelium; 3=1 to 5 small ulcers with a diameter greater than 3 mm; 6=perforated ulcer.

The results of this test were the following:

| Compound | Dosage (mg/Kg weight) | Score | Increase |
|---|---|---|---|
| Control (distilled water) | — | 2.0 | — |
| Phenylbutazone | 75 | 4.3 | 2.3 |
| 2(3'-trifluormethylanilino) pyridine-3-carboxylic acid | 47 | 3.3 | 1.3 |
| Acetylsalicylic acid | 200 | 3.9 | 1.9 |
| Phthalidyl 2(3'-trifluormethylanilino)-pyridine-3-carboxylate | 69 | 2.0 | — |

In accordance with these results not only is the phthalidyl 2-(3'-trifluormethylanilino)-pyridine-3-carboxylate less ulcerogenic than respective acid but it has an antiinflammatory activity greater than the acid. Having proved that the new derivative is a compound orally well tolerated various pharmaceutical forms were prepared. In them the amount of active drug mixture with therapeutically inactive carrier, was in the range of 5 to 60%. For tablets, the used carrier was a mixture of microcrystalline cellulose, povidone, corn starch, talc. For capsules: magnesium stearate, lactose, talc. For suspension: saccharose, methylparabene, propylparabene, raspberry flavour, and colorant. The compound described in this application, or its salts, can be administered in a dosage which contains the equivalent of 0,25 to 1 g of 2-(3'-trifluormethylanilino) nicotinic acid. This invention will now be illustrated by the following specific examples:

EXAMPLE I 49 ml of triethylamine were added to a suspension of 2(3'-trifluormethylanilino) nicotinic acid (70.6 g in 250 ml of dimethylformamide). After stirring for 30 minutes 53.3 g of 3-bromophthalide were added. The reaction mixture was maintained at 25°–30° C. during 4 hr. Ethyl acetate (750 ml) was poured into the reaction mixture. This solution was filtered and extracted with water (4×250 ml), discarding the water layer.

The organic layer was dried with anhydrous mangesium sulfate and then filtered. The solution was concentrated under vacuum at 30°–35° C. until reduced to half of its original volume and then cooled to 5° C. to allow the crystallization of the compound. Thus, the cake was filtered, washed with cool ethyl acetate, and dried under vacuum. Yield: 74% (76.7 g) of phthalidyl ester of 2-(3'-trifluormethylanilino)-pyridin-3-carboxylic acid, m.p.: 165°–167° C.

I.R. (Nujol): absorption band 3300, 1785, 1695, 1610, 1570, 1520, 1340, 1320, 1260, 1160, 1120, 1090, 1050 and 970 cm$^{-1}$.

Elemental Analysis for $C_{21}H_{13}F_3N_2O_4$; Theoretical: C 60.8%; H 3.16%; N 6.76%. Founded: C 61.04%; H 3.42%; N 6.72%.

EXAMPLE II

Triethylamine (20 ml) and 3-bromophthalide (21.3 g) were added to a suspension of 2(3'-trifluormethylanilino)-nicotinic acid (28,2 g in 500 ml of acetone). The mixture was refluxed during 4 hours. The obtained greenish yellow suspension was poured into 6000 ml of water, which was previously heated at 50° C. The stirred reaction mixture was cooled to 5° C., and the formed precipitate was filtered and washed with cool water. Yield: 52% (20.5 g) of phthalidyl 2-(3'-trifluormethylanilino)-pyridin-3-carboxylate, m.p: 162°–164° C.

Applying thin layer chromatography, only one spot appeared in the chromatogram (silicagel; benzene-ethanol/100:2/). IR spectrum was equivalent to IR spectrum of the compound obtained following the example I.

EXAMPLE III

Phthalidyl ester of 2-(3'-trifluormethylanilino)-pyridine-3-carboxylic acid (10 g) was dissolved in warmed ethyl acetate (200 ml). 3 g of an isopropanolic solution of 32.3% of hydrochloric acid was added. The stirred reaction mixture was cooled to 5° C. during 1 hour.

The formed precipitate was filtered and washed with ethyl acetate (2×10 ml).

Yield: 80% (8.75 g) of phthalidyl 2-(3'-trifluormethylanilino)-pyridine-3-carboxylate hydrochloride, m.p.: 158°–160° C. Chlorine amount: 7.93% (theoretical 7.86).

What we claim is:

1. A compound selected from the group consisting of phthalidyl 2-(3'-trifluoromethyl-anilino)-pyridine-3-carboxylate and the pharmacentically acceptable salts thereof.

2. The compound of claim 1 which is phthalidyl 2-(3'-trifluoromethyl-anilino)-pyridine-3-carboxylate.

3. The compound of claim 1 which is phthalidyl 2-)3'-trifluoromethyl-anilino)-pyridine 3-carboxylate hydrochloride.

4. The compound of claim 1 which is phthalidyl 2-(3'-trifluoromethyl-anilino)-3-pyridine-3-carboxylate hydrobromide.

5. A pharmaceutical dosage form adapted to systemic administration to obtain anti-inflammatory effects, which comprises, an effective amount for said effects of a compound selected from the group consisting of phthalidyl 2-(3'-trifluoromethyl-anilino)-pyridine-3-carboxylate and the pharmaceutically acceptable salts thereof; in combination with pharmaceutical means which adapt the compound for systemic administration.

6. The pharmaceutical dosage form of claim 5 wherin said systemic administration comprises oral administration.

7. The pharmaceutical dosage form of claim 5 wherein the effective amount is in the range of 5 to 60 percent by weight of the form.

8. The pharmaceutical dosage form of claim 5 wherein the compound selected is phthalidyl 2-(3'-trifluoromethyl-anilino)-pyridine-3-carboxylate.

9. The pharmaceutical dosage form of claim 5 wherein the compound selected is phthalidyl 2-(3'-trifluoromethyl-anilino)-pyridine-3-carboxylate hydrochloride.

10. A method of treating inflammatory processes in a mammal suffering from such a process, which comprises; administering systemically to said mammal, an antiinflammatory amount of a compound selected from the group consisting of phthalidyl 2-(3'-trifluoromethyl-anilino)-pyridine-3-carboxylate and the pharmaceutically acceptable salts thereof.

11. The method of claim 10 wherein said administration is orally.

12. The method of claim 10 wherein said anti-inflammatory amount is its equivalent of 0.25 to 1 gm. of 2-(3'-trifluoromethyl-anilino nicotinic acid.

13. The method of claim 10 wherein the compound selected is phthalidyl 2-(3'-trifluoromethyl-anilino)-pyridine-3-carboxylate.

14. The method of claim 10 wherein the compound selected is a pharmaceutically acceptable salt of phthalidyl 2-(3'-trifluoromethyl-anilino)-pyridine-3-carboxylate.

* * * * *

UNITED STATES PATENT AND TRADEMARK OFFICE
CERTIFICATE OF CORRECTION

PATENT NO. : 4,168,313
DATED : September 18, 1979
INVENTOR(S) : Sebastian Bago

It is certified that error appears in the above—identified patent and that said Letters Patent are hereby corrected as shown below:

At Column 1, line 28, - "use" should read -- used --

At Column 2, line 22, - "No. 6,703,522" should read -- No. 6,703,552 -- .

Signed and Sealed this

*Twenty-ninth* Day of *January 1980*

[SEAL]

*Attest:*

SIDNEY A. DIAMOND

*Attesting Officer*     *Commissioner of Patents and Trademarks*